(12) United States Patent
Biteau et al.

(10) Patent No.: US 7,867,577 B2
(45) Date of Patent: Jan. 11, 2011

(54) SULFUR MODIFIED SILANES FOR THE ELABORATION OF HIGH REFRACTIVE INDEX MATERIALS

(75) Inventors: John Biteau, St. Petersburg, FL (US); Herbert Mosse, Lutz, FL (US)

(73) Assignee: Essilor International (Compagnie Generale d'Optique) (FR)

( * ) Notice: Subject to any disclaimer, the term of this patent is extended or adjusted under 35 U.S.C. 154(b) by 92 days.

(21) Appl. No.: 12/121,278

(22) Filed: May 15, 2008

(65) Prior Publication Data
US 2009/0287015 A1   Nov. 19, 2009

(51) Int. Cl.
*C08J 7/04*   (2006.01)
*C23C 16/24*   (2006.01)

(52) U.S. Cl. .................. 427/489; 427/588; 427/593; 556/427

(58) Field of Classification Search .................. 556/427; 427/489, 588, 593
See application file for complete search history.

(56) References Cited

U.S. PATENT DOCUMENTS

| | | | |
|---|---|---|---|
| 3,984,606 A | 10/1976 | Morgan | |
| 6,624,237 B2 | 9/2003 | Biteau et al. | |
| 2003/0165698 A1 | 9/2003 | Vaneeckhoutte et al. | |
| 2004/0149966 A1 | 8/2004 | Misura et al. | |
| 2005/0123771 A1 | 6/2005 | Vaneeckhoutte et al. | |
| 2006/0094892 A1 * | 5/2006 | Yanagisawa et al. | 556/400 |

FOREIGN PATENT DOCUMENTS

| | | | |
|---|---|---|---|
| JP | 59-70693 | * | 4/1984 |
| WO | 9425406 | | 11/1994 |

* cited by examiner

*Primary Examiner*—Porfirio Nazario Gonzalez
(74) *Attorney, Agent, or Firm*—Keusey & Associates, P.C.

(57) ABSTRACT

A composition having a polythiol reactant and an alkenyl silane reactant which are combined to form a polysulfide polysilane. In the process, the reactants are combined in a thiol-ene addition process driven by UV radiation. The polysulfide polysilane is then hydrolyzed and may be combined with other hydrolyzed compounds. For coatings, the polysulfide polysilane is hydrolyzed and may optionally be combined with nanoparticles. For bulk materials, the polysulfide polysilane is hydrolyzed, concentrated and heated to form a high refractive index material which can be used to form lenses.

20 Claims, No Drawings

SULFUR MODIFIED SILANES FOR THE ELABORATION OF HIGH REFRACTIVE INDEX MATERIALS

RELATED U.S. DISCLOSURE DOCUMENT

This application further relates to disclosure in U.S. Disclosure Document No. 600,640, filed on May 15, 2006, that is entitled "High Refractive Index Silane from Thiol-ene Chemistry", the entire contents of which is incorporated herein by reference thereto.

BACKGROUND OF THE INVENTION

1. Field of the Invention

The present invention relates generally to high refractive index materials, and processes for synthesizing them, and applications for using them as optical bulk materials or high index hard coats.

2. The Prior Art

For ophthalmic lenses, plastic materials represent a safer, thinner and lightweight alternative. Such plastic ophthalmic lenses frequently have a surface coating to provide scratch resistance or to impart functional optical features such as tints or anti-reflective surfaces.

Silane based matrices can be used for both coatings and bulk materials. These silanes have reasonably good mechanical properties, but suffer from relatively low refractive index (RI) values, between 1.42 and 1.55. As the demand for thinner and lighter lenses increases, there is a greater need for materials having a higher index of refraction and better mechanical properties. The eye lens industry is focusing on producing high index lenses (refractive index, about 1.6-1.7), which require correspondingly high refractive index (1.63-1.68) coatings. The refractive index of presently available organic coatings is about 1.5, making them unsuitable for high index lenses. Therefore, there is an immediate need for optical grade coatings that have high refractive index.

Plastic lens usually have refractive index as high as 1.67, 1.74 or even 1.80. Conventional coatings usually have a low refractive index of about 1.50. The large difference between the lens substrate refractive index and the coating refractive index causes unsightly fringes. Therefore, it would be desirable to have higher index coatings, and hybrid coatings with correspondingly improved mechanical properties.

One prior hybrid coating is disclosed in US Published Application 2005/0123771. An epoxy silane is hydrolyzed and combined with colloidal silica and an aluminum compound, like an aluminum chelate. The composition has application as an abrasion resistant coating and is useful when applied in conjunction with nonreflective coating layers. Another prior art example is described in US Published Application 2003/165698.

An example of prior art bulk materials is the class of organic polymers. Organic polymers based on thiols and thioethers provide a high refractive index (up to 1.70) but are purely organic and not hybrid organic-inorganic. Mechanical properties can be improved by introducing inorganic nanoparticles, however the resulting material is usually hazy due to nanoparticles aggregation.

Hybrid materials, such as transparent hybrid bulk materials are known to be made from silanes leading to an inorganic network. In that case the refractive index is low. The refractive index can be increased slightly by introducing metal alkoxides. However in this case huge differences in kinetics lead to precipitation of the metal alkoxide, limiting the per cent of metal alkoxide content or leading to hazy materials. A prior bulk material is disclosed in U.S. Pat. No. 6,624,237 by hydrolyzing an organo-silicon monomer. The monomer may be combined with an epoxy silane or photochromic compound before hydrolyzing. Another prior art example is described in WO94/25406, which discusses the sol-gel process.

An example of prior art silane coatings is glycidoxypropyltrimethoxysilane, which is referred to by the commercial name Glymo. Glymo is a precursor that is currently used for abrasion resistant coatings in the ophthalmic industry. A high crosslinking rate is achieved, but its refractive index is limited to 1.51. Higher refractive index coatings are obtained by adding high refractive index nanoparticles, such as $TiO_2$ or $ZrO_2$. Such coatings are limited in refractive index due to the low RI of the Glymo. When the content of high RI nanoparticles is increased the coatings becomes brittle and mechanical performance is reduced.

Accordingly, it is an object of the present invention to provide a new class of materials, and their applications as high refractive index bulk materials and coatings.

SUMMARY OF THE INVENTION

It is therefore an object of the present invention to provide a specific class of two reactants which combine to form a polysulfide polysilane, a high refractive index precursor material.

It is another object of the invention to hydrolyze the polysulfide polysilane to form a coating, and by optionally combining another silane or Glymo before hydrolysis and optionally adding inorganic nanoparticles after hydrolysis.

It is another object of the invention to hydrolyze the polysulfide polysilane followed by a sol-gel process and heating to provide a transparent, dense material suitable for use as bulk optical materials such as lenses.

It is a further object to describe a process for synthesizing the polysulfide polysilane, which includes a thiol-ene addition process.

It is another object to specify additional hydrolyzing steps to provide a hydrolyzed product or a mixture of hydrolyzed compounds.

It is yet another object to describe additional hydrolyzing steps with the optional addition of silanes such as Glymo before the hydrolysis or the optional addition of inorganic nanoparticles after hydrolysis to form high refractive index coatings.

It is a further object to specify another hydrolysis step followed by a sol-gel and heating step to provide a transparent dense material suitable for use as bulk materials for optical lenses.

For the product embodiment of the invention, we propose sulfur modified silanes for the elaboration of high refractive index materials. A polysulfide polysilane is synthesized as the reaction product of a polythiol (I) and an alkenyl silane (II). The polythiol (I) has a formula,

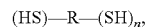

wherein n is an integer between 1 and 5 inclusive; and

R is a group selected from:
  arylene,
  heteroarylene,
  and linear or branched ($C_1$-$C_{30}$)alkylene, wherein from 1 to 10 carbon atoms may be replaced by a group selected from (CO), ($SO_2$), $NR_4$ where $R_4$ represents a hydrogen atom or linear or branched ($C_1$-$C_6$)alkyl, O, S, or P; and/or each alkylene group may be optionally substituted by a group selected from hydroxyl, carboxy, aryl, and heteroaryl, these two last groups may be substituted onto the said alkylene chain at a terminal position or inside the alkylene chain.

The alkenyl silane (II) has the formula

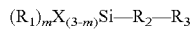

$(R_1)_m X_{(3-m)} Si—R_2—R_3$ wherein:
R$_1$ is a linear or branched (C$_1$-C$_{10}$)alkyl group, which comprised optionally from 1 to 5 heteroatoms selected from NR$_4$ where R$_4$ represents a hydrogen atom or linear or branched (C$_1$-C$_6$)alkyl, O, S, or P; and/or each alkyl group may be optionally substituted by a group selected from hydroxyl, carboxy, and (C$_1$-C$_6$)alkoxy;

X is a group selected from a halogen atom, and —OR$_5$, wherein R$_5$ represents a group selected from:
(C$_3$-C$_{10}$)cycloalkyl, (C$_3$-C$_{10}$)heterocycloalkyl, and linear or branched (C$_1$-C$_6$)alkyl which may be comprised from 1 to 3 heteroatoms selected from the group consisting of NR$_4$ where R$_4$ represents a hydrogen atom or linear or branched (C$_1$-C$_6$)alkyl, O or S; and/or each alkyl group may be substituted by a group selected from linear or branched (C$_1$-C$_6$)alkoxy, carboxy, and hydroxy;

m is an integer between 0 and 2 inclusive;

R$_2$ is either absent or represented by a group selected from: linear or branched (C$_1$-C$_{10}$)alkylene wherein from 1 to 4 carbon atom may be replaced by a group selected from (CO), NR$_4$ where R$_4$ represents a hydrogen atom or linear or branched (C$_1$-C$_6$)alkyl, O or S; and/or each alkylene group may be optionally substituted by a group selected from linear or branched (C$_1$-C$_6$)alkoxy, carboxy, and hydroxy;

R$_3$ represents a group selected from linear or branched (C$_1$-C$_{10}$)alkenyl, (C$_4$-C$_{10}$)cycloalkenyl, and (C$_4$-C$_{10}$) heterocycloalkenyl, each of these groups may be optionally substituted by a group selected from linear or branched (C$_1$-C$_6$)alkyl, linear or branched (C$_1$-C$_6$) alkoxy, linear or branched (C$_1$-C$_6$)thioalkoxy, carboxy, thiol, and hydroxyl.

In the present application the following definitions apply:

Aryl means monocyclic or polycyclic aromatic group which comprise from 4 to 14 carbon atoms and is optionally substituted by a group selected from hydroxy, linear or branched (C$_1$-C$_6$)alkyl, linear or branched (C$_1$-C$_6$)alkoxy, and carboxy. In accord with this meaning, the following aryl group could be mentioned, for example, phenyl, naphtyl, acenaphtenyl, biphenylenyl, anthracyl. According to the invention, the preferred aryl group represents a phenyl group.

Heteroaryl means an aryl group as defined hereinbefore and wherein at least one carbon atom, and preferentially from 1 to 4 carbon atom, of the monocyclic or polycyclic is replaced by an heteroatom selected from O, N, and S. In accord with this meaning the following heteroaryl could be mentioned, for example, pyrimidyl, furyle, thienyl, thiadiazolyl, oxadiazolyl.

Halogen atom means an atom selected from Cl, Br, F and I.

In the definition of compounds of formula (I) and (II), when it is mentioned that a group may be "substituted", it may be understood that in preferred embodiments such a group comprises from 1 to 4 substituents.

The polythiols (I) preferably have between 2 to 6 thiol groups inclusive, and more preferably from 2 to 4 thiol groups inclusive. In the polythiols, R comprises preferentially from 1 to 20 carbon atoms, and when a heteroatom is presented in the R group is preferentially a sulfur atom. Then in a first preferred embodiment, the compound of formula (I) has a ratio of S atoms to C atoms (nS/nC) that is at least 1 over 4 (nS/nC=¼). This means that in the preferred compound of formula (I), there is at least 1 sulfur atom for 4 carbon atoms. In another preferred embodiment of tire polythiol, R comprises preferentially from 1 to 10 carbon atoms, and from 1 to 6 sulfur atoms. Then in this preferred embodiment the compound of formula (I) has a ratio of S atoms to C atoms (nS/nC) is at least 1 over 2. This means that in the preferred compound of formula U), there is at least 1 sulfur atom for 2 carbon atoms.

The polythiol may be selected, for example, from the following compounds: 1,2-ethanedithiol; 1,3-propanedithiol; 1,4-butanedithiol; 1,2-butanedithiol; 1,5-pentanedithiol; 1,6-hexanedithiol; 1,8-octanedithiol; 2,2'-oxydiethanethiol; 3,6-dioxa-1,8-octanedithiol; ethylene glycol bisthiol-glycolate; dl-1,4-dithiothreitol; 2,2'-thiodiethanethiol; bis(2-mercaptoethyl)sulphone; 2,5-dimercapto-1,3,4-thiadiazole; 5-( {2-[(5-mercapto-1,3,4-thiadiazol-2-yl)thio]ethyl}thio)-1,3,4-thiadiazole-2-thiol; pentaerythritol tetra(2-mercaptoacetate); trimethylolpropane tris(3-mercaptopropionate); trimethylolpropane tris(2-mercaptoacetate); 1,4-benzenedithiol; 1,3-benzenedithiol; 3,4-dimercaptotoluene; 1,4-benzenedimethanethiol; 1,3-benzenedimethanethiol; 1,6-di (methanethiol)-3,4-dimethyl-phenyl; [3-(mercaptomethyl)-2,4,6-trimethylphenyl]methanethiol; 1,5-dimercaptonaphthalene; 3,3'-thiobis[2-[(2-mercaptoethyl) thio]-1-propanethiol; 5-[3-(5-mercapto-1,3,4-oxadiazole-2-yl)propyl]-1,3,4-oxadiazole-2-thiol; 1,3,5-triazine-2,4,6(1H, 3H,5H)-trithione; and 2,3-bis[(2-mercaptoethyl)thio]-1-propanethiol.

A preferred form of the alkenyl silane is where m is zero, X is an alkoxy group, and R$_2$ is absent or represents a (C1-C3) alkylene group Preferably, the alkenyl silane is vinyltrimethoxysilane. The synthesized polysulfide polysilanes (III), obtained by thiol-ene addition, possesses a refractive index in the range comprises from 1.47 to 1.55. These polysulfide polysilanes (III), may be hydrolized to form an optical coating (IVa).

The polysulfide polysilanes (III) may be also mixed with another silane, which could be Glymo, for example or another polysulfide polysilane (III) and then hydrolyzed to form an optical coating (IVb).

Nanoparticles made from inorganic oxides may optionally be added after the hydrolysis step to either optical coating (IVa) or (IVb). The amount of nanoparticles may be comprised between 20% and 80% of the weight of the optical coating. nsis results in an optical coating having a refractive index in the range from 1.59 to 1.67, or greater.

The polysulfide polysilanes (III) may be also hydrolyzed, concentrated and then heated to form a bulk material M. The said bulk material (V) is well suited to form an optical lens which may present a refractive index of at least 1.63.

For the process embodiment of the invention, we propose:
(i) mixing a polythiol (I) and an alkenyl silane (II), of the above types and preferred form(s) to make a solution; and
(ii) exposing the solution to UV radiation to undergo thiol-ene addition to synthesize a polysulfide polysilane (EL). The mixing step (i) may comprise the addition of a further compound, which may be, for example, a catalyst, a photoinitiator, a solvent or combinations thereof.

Following the exposing step (ii), the process comprises a further step (iiia) of hydrolyzing the polysulfide polysilane (III), preferably in the presence of an acid, like HCl to form an optical coating (IVa).

In one embodiment, following the exposing step (ii), the process may include a further step of mixing compound (III) with another silane which may be selected from a silane compound as Glymo, and another polysulfide polysilane (III) and then a step (iiib) of hydrolyzing to form an optical coating (IVb).

According to both of the above embodiments, the process may also comprise after the hydrolysis step (iiia) or (iiib), the addition of nanoparticles made from inorganic oxides, with a range of between 20% to 80% of the weight of the optical coating (IVa) or (IVb).

In another embodiment the process may comprise, following the exposing step (ii), a further step (iv) of hydrolyzing compound (III); concentrating and then heating the hydrolyzed material to form a bulk material (V) which possesses a refractive index of at least 1.63. According to this embodiment the process may also comprise, following the step (iv), a step of adding a catalyst selected from metal chelates or amines.

It is another object of the invention to provide an optical article which is obtained by using a bulk material obtained from these polysulfide polysilanes.

It is yet another object of the present invention to provide an optical article which an optical coating obtained from these polysulfide polysilanes.

These and other aspects, features and advantages of the present invention will be described or become apparent from the following detailed description of preferred embodiments.

DETAILED DESCRIPTION OF PREFERRED EMBODIMENTS

As an overview of the new compound, a polythiol reactant is combined with an alkenylsilane reactant to provide a high index precursor material, which we refer to as polysulfide polysilane.

The polythiols (I) have the general formula:

(HS)—R—(SH)$_n$       (I)

wherein
n is an integer comprise from 1 to 5 inclusive; and
R is a group selected from:
arylene
heteroarylene,
and linear or branched ($C_1$-$C_{30}$)alkylene, wherein from 1 to 10 carbon atoms may be replaced by a group selected from (CO) ($SO_2$), $NR_4$ wherein $R_4$ represents an hydrogen atom or linear or branched ($C_1$-$C_6$)alkyl, O, S, and P; and/or each each alkylene group may be optionally substituted by a group selected from hydroxyl, carboxy, aryl, and heteroaryl, these two last groups may be substituted onto the said alkylene chain at a terminal position or inside the alkylene chain;

In a non-limiting exemplary listing, the following commercially available thiols can be used: 1,2-ethanedithiol; 1,3-propanedithiol; 1,4-butanedithiol; 1,2-butanedithiol; 1,5-pentanedithiol; 1,6-hexanedithiol; 1,8-octanedithiol; 2,2'-oxydiethanethiol; 3,6-dioxa-1,8-octanedithiol; ethylene glycol bisthiol-glycolate; dl-1,4-dithiothreitol; 2,2'-thiodiethanethiol; bis(2-mercaptoethyl)sulphone; 2,5-dimercapto-1,3,4-thiadiazole; 5-({2-[(5-mercapto-1,3,4-thiadiazol-2-yl)thio]ethyl}thio)-1,3,4-thiadiazole-2-thiol; pentaerythritol tetra(2-mercaptoacetate); trimethylolpropane tris (3-mercaptopropionate); trimethylolpropane tris (2-mercaptoacetate); 1,4-benzenedithiol; 1,3-benzenedithiol; 3,4-dimercaptotoluene; 1,4-benzenedimethanethiol; 1,3-benzenedimethanethiol; 1,6-di(methanethiol)-3,4-dimethyl-phenyl; [3-(mercaptomethyl)-2,4,6-trimethylphenyl]methanethiol; 1,5-dimercaptonaphthalene; 3,3'-thiobis[2-[(2-mercaptoethyl)thio]-1-propanethiol; 5-[3-(5-mercapto-1,3,4-oxadiazole-2-yl)propyl-1,3,4-oxadiazole-2-thiol; 1,3,5-triazine-2,4,6(1H,3H,5H)-trithione; and 2,3-bis[(2-mercaptoethyl)thio]-1-propanethiol.

Preferred polythiols will be those that can be formed into polysulfide polysilanes having a high refractive (RI) index. For example, those resulting in an RI of about 1.47 or greater, and more preferably above 1.55. Exemplary polythiols which produce such RI values are trimethylolpropane tris(2-mercaptoacetate), 2-mercaptoethyl sulfide, 3,6-dioxa-1,8-octanedithiol, ethylene glycol bisthiol-glycolate, and trimethylolpropane tris(3-mercaptopropionate).

In practical tests described in greater detail below, 3,3'-thiobis[2-[(2-mercaptoethyl)thio]-1-propanethiol and trimethylolpropane tris (2-mercaptoacetate) emerged as preferred polythiols. Another way to classify preferred polythiols, are those having a high nS/nC ratio. For example a ratio of 5/10 or more preferably a ratio of 7/10 or greater.

The alkenyl silane reactant (II), can be presented by the general formula:

($R_1$)$_m$$X_{(3-m)}$Si—$R_2$-$R_3$       (II)

wherein:
$R_1$ is a linear or branched ($C_1$-$C_{10}$)alkyl group, which comprised optionally from 1 to 5 heteroatoms selected from $NR_4$ where $R_4$ represents a hydrogen atom or linear or branched ($C_1$-$C_6$)alkyl, O, S, or P; and/or each alkyl group may be optionally substituted by a group selected from hydroxyl, carboxy, and ($C_1$-$C_6$)alkoxy;

X is a group selected from halogen atom, and —$OR_5$, wherein $R_5$ represents a group selected from ($C_3$-$C_{10}$)cycloalkyl, ($C_3$-$C_{10}$)heterocycloalkyl, and linear or branched ($C_1$-$C_6$)alkyl which may be comprised from 1 to 3 heteroatoms selected from the group consisting of NR4 wherein $R_4$ represents an hydrogen atom or linear or branched ($C_1$-$C_6$)alkyl, O or S; and/or each alkyl group maybe substituted by a group selected from linear or branched ($C_1$-$C_6$)alkoxy, carboxy, and hydroxy;

m is an integer between 0 and 2 inclusive;

$R_2$ is either absent or represented by a group selected from:

linear or branched ($C_1$-$C_{10}$)alkylene wherein from 1 to 4 carbon atom may be replaced by a group selected from (CO), $NR_4$ wherein $R_4$ represents an hydrogen atom or linear or branched ($C_1$-$C_6$)alkyl, O or S; and/or each alkylene may be optionally substituted by a group selected from linear or branched ($C_1$-$C_6$)alkoxy, carboxy, and hydroxy;

$R_3$ represents a group selected from linear or branched ($C_1$-$C_{10}$)alkenyl, ($C_4$-$C_{10}$)cycloalkenyl, and ($C_4$-$C_{10}$)heterocycloalkenyl, each of these groups may be optionally substituted by a group selected from linear or branched ($C_1$-$C_6$)alkyl, linear or branched ($C_1$-$C_6$)alkoxy, linear or branched ($C_1$-$C_6$)thioalkoxy, carboxy, thiol, and hydroxyl.

In a non limiting embodiment, the following silanes could be used as a reactant in the reaction with the polythiol: vinylphenylmethymethoxysilane, vinylphenylmethylchlorosilane, vinylphenyldiethoxysilane, vinylphenyldichlorosilane, 10-undecenyltrimethoxysilane, 10-undecenyltrichlorosilane, 10-undecenyldimethylchlorosilane, 7-octenyltrimethoxysilane, 7-octenyltrichlorosilane, 7-octenyldimethylchlorosilane, allyltrimethoxysilane, allyltriethoxysilane, allyltrichlorosilane, allylphenyldichlorosilane, allyloxyundecyltrimethoxysilane, allylmethyldichlorosilane, allyldimethylchlorosilane, allyldimethoxysilane, allyldichlorosilane, allyl(chloropropyl)dichlorosilane, allyl(chloromethyl)dimethylsilane, 3-(n-allylamino)propyltrimethoxysilane, butenyltriethoxysilane, butenylmethyldichlorosilane, 5-hexenyltrichlorosilane, 5-hexenyldimethylchlorosilane, hexenyltriethoxysilane, vinyltriisopropoxysilane, vinyltris(methoxypropoxy)silane, vinyltris(2-methoxyedioxy)silane, vinyltriphenoxysilane, vinyltrimethoxysilane, vinyltriethoxysilane, vinyltrichlorosilane, vinyltri-t-butoxysilane, vinyltriacetoxysilane, vinyloctyldichlorosilane, vinylmetlhyldimethoxysilane, vinylmethyldiethoxysilane, vinylmethyldichlorosilane, vinylmethyldiacetoxysilane, 3-cyclohexenyltrichlorosilane, [2-(3-cyclohexenyl)ethyl]triethoxysilane, 3-(trimethoxysilyl)propyl methacrylate.

Preferred silanes will be those that can form into polysulfide polysilanes having a high refractive(RI) index. For example, those resulting in an RI of about 1.47 or greater, and more preferably above 1.5. In a practical test described in greater detail below, vinyltrimethoxysilane emerged as a preferred silane since it provided a polysulfide polysilane having an RI of 1.509. Another way to classify desirable silanes, are those wherein, m is zero, X is an alkoxy group, and $R_2$ is absent or represents a (C1-C3)alkylene group.

The two reactants are combined and the thiol-ene addition reaction is driven by exposing the mixture to UV radiation to produce a polysulfide polysilane (III). Accordingly, the first aspect of our invention is the process for preparing such a polysulfide polysilane, along with the polysulfide polysilane composition itself The thiol-ene addition reaction may be cared out upon stoichiometric quantities of the reactants. For Example 1, the quantities would be represented by one stoichiometric quantity of 3,3'-thiobis[2-[(2-mercaptoethyl)thio]-1-propanethiol or MIR10B and four stoichiometric quantities of vinyltrimethoxysilane or VTMOS. Non-stoichiometric quantities can be employed. Excess quantities of alkenyl silane (III) may be utilized to maximize the yield of the thiol-ene addition. When an excess of alkenyl silane is used for tie thiol-ene addition, the product of the reaction may be purified or the reaction mixture used as is for hydrolysis. The hydrolysis step may be performed in a separate stage from the one or more thiol-ene addition stage reactions. Alternately, it may be possible to perform the thiol-ene addition and hydrolysis in a single stage, in a so-called "one pot reaction." The thiol-ene addition can be carried out under normal atmospheric conditions, while an inert atmosphere is preferred. The thiol-ene addition can be carried out at room temperature. Certain reactions are exothermic, and it may be preferable to cool the mixture.

The composition may contain no photoinitiator or optionally at least 1 photoinitiator. Those skilled in the art are aware that the thiol-ene reaction can be initiated by one of several techniques. To facilitate the reaction, one may add a photoinitiator. Among conventional photoinitiators the following can be used: benzophenones, acetophenone derivatives like α-hydroxyalkylphenylketones, benzoin alkyl ethers, benzylketals, monoacylphospline oxides, bisacylphosphine oxides. When used the photoinitiators are present in a low amount such as lower that 1 weight %, preferably lower than 0.05% and even more preferably lower than 0.02%. Most preferably no photoinitiator is used. If the photoinitiator can increase the rate of reaction, it also tends to increase yellowing of the composition and thus leads to the need of purification after synthesis of the polysulfide polysilane. Preferably the thiol-ene reaction is conducted without a photoinitiator. However, the first aspect of our invention also includes a process and polysulfide polysilane composition in which a photoinitiator or catalyst is present.

In some specific cases a solvent might optionally be used. In such cases the solvents used are preferably not interacting with the thiol-ene reaction. These solvents are preferably non protic. Insaturations like carbon double bonds should be avoided. A solvent can be used when the 2 reactants are not miscible and/or when one of the 2 reactants is solid at the temperature at which the reaction is taking place. An example of solvent which might be used optionally is tetrahydrofuran. The first aspect of our invention additionally includes a process in which a solvent is present and the resulting polysulfide polysilane composition.

The polysulfide polysilane (III) is then partially or completely hydrolyzed. Optionally, other silanes may be added prior to hydrolyzing. Such additional silanes can be another polysulfide polysilane (also produced by the thiol-ene reaction or can be any other silane, such as Glymo. In a preferred embodiment the other silane is another polysulfide polysilane (II). Accordingly, the second aspect of our invention is the process For completely or partially hydrolyzing the polysulfide polysilane. The second aspect optionally includes hydrolyzing a blend of polysulfide polysilanes or other silanes, in the presence of an acidic aqueous solution or a basic aqueous solution. The use of an acidic aqueous solution is preferred for the hydrolysis, in order to better control and separate the hydrolysis and the condensation steps. This acidic solution may be an acidic water solution (HCl in $H_2O$). The second aspect also includes all the resulting products from hydrolyzing with the various options discussed.

COATINGS—To form an optical coating, the polysulfide polysilane (III) is hydrolyzed. Prior to hydrolyzing, another polysulfide polysilane or silane such as Glymo may be mixed with polysulfide polysilane (III). The hydrozolate can be used as a coating with or without additional compounds. After hydrolyzing, a colloid, as a nanoparticles-contributing source, may be added. In certain cases, a solvent may be added. The hydrolyzed material with nanoparticles may be used as a high index hard coat for optical products, such as lenses. The colloid may include an inorganic oxide selected from the group consisting of silicon dioxide (silica), aluminum oxide (alumina), antimony oxide, tin oxide, titanium oxide, zirconium oxide and mixtures of such inorganic oxides.

The inorganic oxide may be in the form of a colloid. As used in the present specification, the term sol means and includes a colloidal dispersion of finely divided solid inorganic inorganic oxide particles in an aqueous or an organic liquid. It is preferable that the inorganic oxide maintains a stable dispersion state in the matrix and/or a low haze level, therefore, the average size of such particles may range from 1 to 200 nanometers, preferably from 2 to 100 nanometers, and more preferably, from 5 to 50 nanometers.

Examples of the above inorganic oxide include $SiO_2$, $Al_2O_3$, $SnO_2$, $Sb_2O_5$, $Ta_2O_5$, $CeO_2$, $La_2O_3$, $Fe_2O_3$, ZnO, $WO_3$, $ZrO_2$, $In_2O_3$ and $TiO_2$ alone or by mixture of at least two of them.

The inorganic oxides have a refractive index of from 1.7 to 3.0, and more preferably may be a multi-component oxide(s) including two or more compounds selected from the group consisting of $TiO_2$ (refractive index: 2.5-2.7), $SiO_2$ (refractive index: 1.5), $ZrO_2$ (refractive index: 2.2), $SnO_2$ (refractive index: 2.0), $Ce_2O_3$ (refractive index: 2.2), $BaTiO_3$ (refractive index: 2.4), $Al_2O_3$ (refractive index: 1.73), and $Y_2O_3$ (refractive index: 1.92). Said multi-component oxide(s) may be composed at adequate contents by their refractive index, and more preferably, at least one of $TiO_2$—$ZrO_2$—$SnO_2$, $TiO_2$—$ZrO_2$—$SiO_2$ and $TiO_2$—$SnO_2$—$SiO_2$ may be used. Preferred multi-component oxide is Optolake I120z(S-95-A8)® that is a TiO$_2$—ZrO$_2$—SiO$_2$ composite with core-shell structure.

This third aspect of the invention, includes processes for preparing a coating, the coating itself, and applications for coating optical articles, such as lenses. The process according to the third aspect includes optionally adding another silane, such as Glymo, before the hydrolysis step. The process also includes optionally adding colloids in the form of inorganic oxides or nanoparticles after the hydrolysis step. The resulting hydrolyzed coatings may include one or more polysulfide polysilane made according to aspect one; may include Glymo or other silanes; and may include colloids. A catalyst can optionally be added to the coating. Nanoparticles may optionally be added to the coating. The applications include dip-coating, spin-coating, flow, fan-coating, spray coating and other lens coating techniques. Dip-coating and spin-coating are industrially cost effective and are the preferred techniques. After the coating is applied to the lens, it is cured and crosslinked to form a solid, hard coat.

The coatings may be applied to a wide variety of lens substrate materials. The substrates may be selected from mineral glass and also organic glass made of, for example, polycarbonate, polyamide, polyimide, polysulfone, copolymers of polyethyleneterephthalate and polycarbonate, polyolefine, homopolymers and copolymers of diethylene glycol bis(allylcarbonate), homopolymers and copolymers of (meth) acrylic monomers, homopolymers and copolymers of thio (meth)acrylic monomers, homopolymers and copolymers of urethane, homopolymers and copolymers of thiourethane, epoxy homopolymers and copolymers, and episulfure homopolymers and copolymers.

Preferably, the substrate is an organic material, more preferably an organic lens. According to a preferred embodiment of the invention, the substrate is an optic glass or an optical lens which is selected from ophthalmic lens, ocular visor, and sight optical systems. In a preferred embodiment, the substrate is an ophthalmic lens which may be an afocal, a unifocal, a bifocal, a trifocal or a progressive lens. Each ophthalmic lens may be also transparent, solar, or photochromic. In such case, the substrate coated with the abrasion-resistant coating may be overcoated with classical properties enhancing coatings such as anti-reflecting coating and top coat. Anti-reflecting coatings and their methods of making are well known in the art. The top coat, typically a hydrophobic top coat, which in the finished optical article constitutes the outermost coating on the optical substrate, is intended for improving the dirty mark resistance of the finished optical article.

Transparent substrates having a refractive index not smaller than 1.50 include, for examples, those made of polycarbonates which have a refractive index of 1.50. Moreover, a number of resins have been proposed in many patent publications and laid-open applications for use as plastic lenses for glasses, including those lenses made of polyurethane resins, methacrylic polymers, acrylic polymers and combinations thereof. For instance, lenses made of urethane resins are ones which are obtained by thermally curing monomers MR-6, MR-7 and MR-8 (commercially available from Mitsui Toatsu Chemicals Inc.). Lenses made of methacrylic polymers are those obtained by radical polymerization of TS-26 monomer commercially available from Tokuyama Co., Ltd.). Likewise, lenses obtained by use of urethane reaction and vinyl polymerization are those obtained by polymerizing ML-3 monomer (commercially available from Mitsubishi Gas Chemical Co., Inc.).

The coating can be applied to either the convex surface or the concave surface of the lens, or both. The hard coat should preferably have a dry final thickness between about 0.2 microns to about 10 microns. The lens may be treated or contacted with a primer prior to application of the coating layer.

BULK MATERIALS—To form bulk materials, the hydrolyzed product is subject to the sol-gel process including evaporation and crosslinking during a carefully controlled heating step leading to a densified and transparent material, as described in U.S. Pat. No. 6,624,237. A typical method for fabricating transparent dense glasses based on silanes using the sol-gel route, may comprise the following steps: A) a complete hydrolysis of a solution containing one or a several silicon alkoxides is carried out in a solvent or a mixture of organic solvents of the alkoxide(s) by using an aqueous acidic solution; B) the organic solvent(s) and the residual alcohols are removed, and the resulting solution is concentrated by distillation under primary vacuum conditions so as to obtain a viscous sol, having for example a concentration of 1-10 moles/l in silicon atoms; C) gelling and air drying or drying in an inert atmosphere are initiated at a temperature lower than 158° F (70° C); D) the glass may be annealed at a temperature lower than 932° F (500° C).

In one embodiment, the sol is slowly evaporated at room temperature and atmospheric pressure for 2 hours (h) to several weeks, preferentially for 15 h. Optionally the partial evaporation is conducted under reduced pressure. In another embodiment the sol or the gel is heated at a temperature between 104° F and 392° F (40° C and 200° C), preferentially between 104° F and 266° F (70° C. and 130° C) for a time comprised between 30 minutes and 3 weeks, preferentially between 4 h and 72 h. Optionally a condensation catalyst is added to the hydrolyzed compound in order to accelerate the crosslinking process.

A specific example is presented below as Example 7. This fourth aspect of the invention includes the process for preparing a bulk material, the bulk material itself and applications for forming the bulk materials into optical articles, such as lenses. The RI of such matrix materials is in the range of at least 1.6, and preferably at least 1.63.

The process according to the invention, will now be discussed in greater detail, by reference to the following examples.

EXAMPLE 1

3,3'-thiobis[2-[(2-mercaptoethyl)thio]-1-Propanethiol (MR10B) and vinyltrimethoxysilane (VTMOS) are mixed together with tetrahydrofuran (THF) solvent to allow initial miscibility. The solution is placed in a vial and exposed to UV irradiation. The thiol-ene addition takes place under UV, without addition of any catalyst. The reaction equation is as follows:

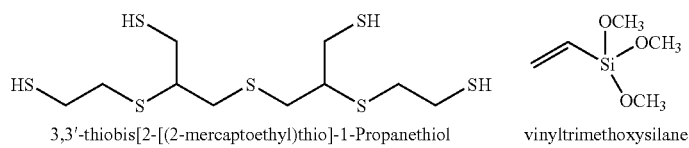

3,3'-thiobis[2-[(2-mercaptoethyl)thio]-1-Propanethiol      vinyltrimethoxysilane -continued

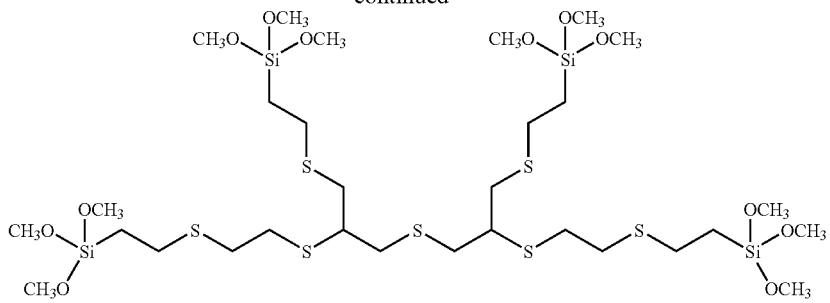

By weight 13.23 g MR10B, 12.45g VTMOS, and 4.32g THF were combined in a glass vial to produce approximately 30 grams of solution. The irradiation step consisted of 5 passes under the Fusion UV source (H Bulb), by a conveyor belt at 4.95cm/s. The resulting polysulfide polysilane has a refractive index of 1.546.

EXAMPLE 2

By weight, 35.65 g of trimethylolpropane tris (2-mercaptoacetate) and 44.47 g vinyltrimethoxysilane (VTMOS) were mixed together and subject to UV radiation consisting of 5 passes under the Fusion UV source (H Bulb), on a conveyor belt at 4.95cm/s. The UV dose was 10.13 J/cm² at an intensity of 3.401 Watts/cm². A solvent was not necessary for miscibility of the VTMOS, but it could be optionally used. The resulting structure is:

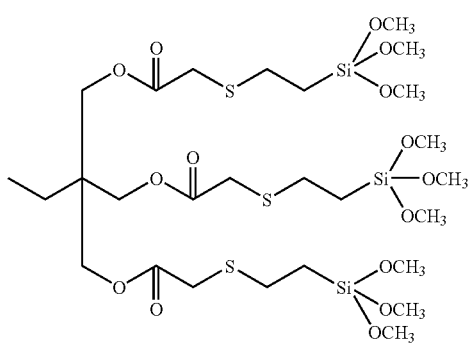

The polysulfide polysilane produced has a refractive index of 1.477.

EXAMPLE 3

Under conditions similar to Example 2, 10 g of 2-Mercaptoethyl Sulfide was combined with 19.22 g of VTMOS to produce the following compound:

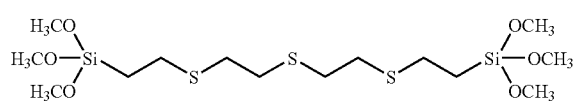

The compound has a refractive index of 1.509.

EXAMPLE 4

Under conditions similar to Example 2, 10 g of 3,6-Dioxa-1,8-Octanedithiol was combined with 16.27 g of VTMOS to produce the following compound:

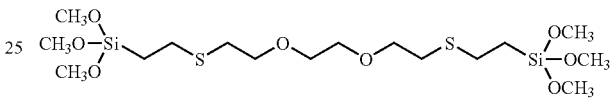

The compound has a refractive index of 1.460.

EXAMPLE 5

Under conditions similar to Example 2, 30 g of Ethylene Glycol Bisthiol-glycolate was combined with 42.23g of VTMOS to produce the following compound:

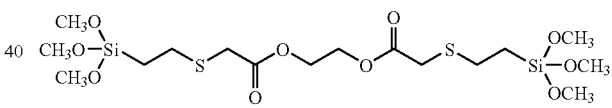

The compound has a refractive index of 1.475.

EXAMPLE 6

Under conditions similar to Example 2, 35.65 g of Trimethylolpropane tris (3-mercaptopropionate) was combined with 49.72 g of VTMOS to produce the following compound:

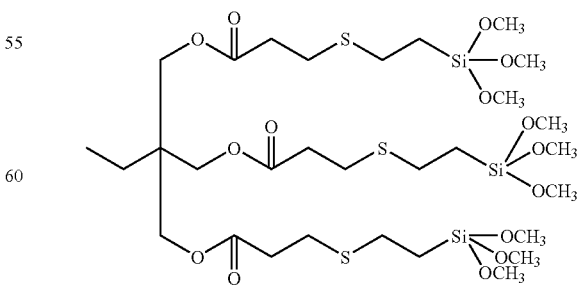

The compound has a refractive index of 1.480.

EXAMPLE 7

The product obtained in Example 1 is hydrolyzed by acidic water solution (HCl in $H_2O$ 1N). The sol-gel process takes place under controlled conditions followed by a heating step, leading to a transparent material. The 2 steps cross-linking stage is made of a $1^{st}$ step of 15h at room temperature followed by 3 days at 212° F (100° C.). The bulk material obtained presents a refractive index equal to 1.63 and an Abbe value of 41. These 2 optical characteristics are measured by ellipsometry and by brewster angle definition at (Metricon) at several wavelength of the visible. The density of this material is 1.38. Accordingly, high refractive index bulk hybrid organic-inorganic material can be formed by hydrolyzing heating the various polysulfide polysilanes to create a highly-crosslinked matrix. The resulting matrix is suitable for use in optical applications, for example lenses, for ophthalmic use.

The various polysulfide polysilanes obtained in the examples 1 to 6 are hydrolyzed to create coating formulations. The following examples are prepared with various types of colloidal nanoparticles oxides.

COATING EXAMPLE 8

The formulation of a coating is made as follows: 20.64 grams of precursor 2 are mixed with 41.21 grams of methanol and stirred till the mixture becomes clear. 4.6 grams of HCl/$H_2O$ (0.1N) are then added over 1 minute while stirring. Once the solution clears 21.0 grams of methanol are immediately added. 29.3 grams of the colloid Optolake 1130Z(S-7-A8) from Catalysts & Chemicals Ind. Co., Ltd. are then slowly added, followed by 3.24 grams of methylethylketone. Finally, 0.01 grams of the surfactant EFKA 3034 are added to the solution.

COATING EXAMPLES 9-13

The formulation is the same as in example 8, but the polysulfide polysilane and the colloid are changed according to Table 1. Each coating is formulated based on 70% by weight of polysulfide polysilane before hydrolysis and 30% by weight of nanoparticles (excluding the dispersion medium of the colloid).

The coating solution is then deposited on lenses made from MR-8 (commercially available from Mitsui Toatsu Chemicals Inc.) by spin coating (for about 5 seconds at 500 rpm followed by 10 s at 750 rpm). Once deposited on a lens the coating is cured at 212° F (100° C.) for 3 hours.

Each coating is characterized, as reported in Table 1, by the refractive index of the matrix (cured in the same condition) without colloid (column 5) and by the refractive index of the coating based on the polysulfide polysilane and the nanoparticles (column 6). It should be understood that any combination of polysulfide polysilanes and colloids can be used together, and that Table 1 simply provides a limited number of exemplary combinations.

TABLE 1

| Example | Example of polysulfide polysilane | $TiO_2$ based High Refractive Index Nanoparticles, from Catalyst & Chemicals Ind. Co., Ltd | RI of the polysulfide polysilane | RI of the matrix after hydrolysis-condensation | RI of a coating made of 70% wt matrix and 30% wt High Index Nanoparticles |
|---|---|---|---|---|---|
| 8 | 2 | 1130Z(S-7-A8) | 1.477 | 1.545 | 1.62 |
| 9 | 1 | 1120Z(11RU-7-A8) | 1.546 | 1.630 | 1.67 |
| 10 | 3 | 1120Z(11RU-7-A8) | 1.509 | 1.587 | 1.62 |
| 11 | 4 | 1120Z(11RU-7-A8) | 1.460 | 1.538 | 1.59 |
| 12 | 5 | 1120Z(11RU-7-A8) | 1.475 | 1.538 | 1.59 |
| 13 | 6 | 1120Z(11RU-7-A8) | 1.480 | 1.552 | 1.60 |

COATING EXAMPLES 14, 15

Coatings 14 and 15 were formulated the same way as the examples 8 to 13. As reported in Table 2, the polysulfide polysilane from example 2 was used and various colloids from different suppliers. When not specified the supplier is Catalyst & Chemicals Ind. Co., Ltd.

The coatings 8, 9, 14 and 15 were also characterized with the Bayer abrasion test. The ASTM Bayer Abrasion resistant measurement is determined by measuring the percent haze of a coated and uncoated lens, before and after testing on an oscillating sand abrader as in ASTM F 735-81. The abrader is oscillated for 300 cycles with approximately 500 g of aluminum oxide ($Al_2O_3$) ZF 152412 supplied by Specially Ceramic Grains. The haze is measured using a Pacific Scientific Hazemeter model XL-211. The ratio of the uncoated lens haze (final-initial) is a measure of the performance of the coating, with a higher ratio meaning a higher abrasion resistance.

TABLE 2

| | polysulfide | Refractive index | | | | |
|---|---|---|---|---|---|---|
| Example | polysilanes from example | polysulfide polysilanes | Matrix | RI of Matrix + Nanoparticles | Colloids | Bayer |
| 9 | 1 | 1.546 | 1.62 | 1.67 | 1120Z(11RU-7-A8)) | ~1 |
| 8 | 2 | 1.477 | 1.545 | 1.623 | 1130Z(S-7-A8) | ~2.25 |
| 14 | 2 | 1.477 | 1.545 | 1.612 | 1120Z(S-95-A8) | ~2 |
| 15 | 2 | 1.477 | 1.545 | 1.567 | Novacentrix $Al_2O_3$ | ~1.5 |

The various Examples demonstrate that the hydrolyzed polysulfide polysilane materials can be further combined with colloids to form a high refractive index coating, which is suitable for coating onto optical articles, for example lenses, for ophthalmic use. The coatings presented herein can be a fill or partial replacement for Glymo where a higher refractive index is desired.

In general, the higher refractive index coating would provide at least the following benefits:
- Use a lower amount of expensive high refractive index colloids;
- Provide a RI above 1.5, preferably above 1.59 and even more preferably above 1.67;
- Use lower refractive index and cheaper colloids for the same refractive index;
- Decrease the haze because of the need of less nanoparticles to reach a given refractive index; and
- Decrease the haze by lowering the refractive index contrast between matrix and high index nanoparticles.

In conclusion, there have been described and shown two classes of reactants which can be combined pursuant to the thiol-ene addition reaction. The resulting polysulfide polysilanes are part of a third class of materials that has been shown and described. This new class of high index precursor materials, has been designated as polysulfide polysilanes. These polysulfide polysilanes are characterized by organic structures which link the sulphur atoms to the silicon atoms, creating a hybrid organic-inorganic material that is highly transparent. The hybrid material combines excellent optical properties, such as low haze, with good mechanical properties. The polysulfide polysilanes can be partially or completely hydrolyzed and then cross-linked through condensation reaction of silanols to form a fourth class of materials. The fourth class includes a mixture of two or more different polysulfide polysilanes made according to the invention.

The polysulfide polysilanes may be hydrolyzed to form optical coatings. Other silanes, for example Glymo, may be combined with polysulfide polysilanes before hydrolysis. Colloids may be added to the hydrolyzed compound.

The polysulfide polysilanes may be hydrolyzed, heated and densified to form a cross-linked bulk material suitable for use as an optical lens. The bulk materials made from the novel polysulfide polysilanes described herein are characterized by a high refractive index, excellent transparency and low density.

It will be understood that certain modifications to the specific details are of utility and may be employed without reference to other features. This is contemplated by and is within the scope of our claims. Although illustrative embodiments of the present invention have been described, it is to be understood that the present invention is not limited to those precise embodiments, and that various other changes and modifications may be affected therein by one skilled in the art without departing from the scope or spirit of the present invention. All such changes and modifications are intended to be included within the scope of the invention as defined by the appended claims.

What is claimed is:

1. An optical article made from a hydrolyzed, concentrated and heated polysulfide polysilane (III), wherein the polysulfide polysilane (III) is obtained by the reaction of:

1) a polythiol (I) represented by the general formula, $$(HS)-R-(SH)_n \qquad (I)$$

wherein
n is an integer between 1 and 5 inclusive; and
R is a group selected from: arylene heteroarylene, and linear or branched $(C_1-C_{30})$alkylene, wherein from 1 to 10 carbon atoms may be replaced by a group selected from (CO), $(SO_2)$, $NR_4$ where $R_4$ represents a hydrogen atom or linear or branched $(C_1-C_6)$alkyl, O, S, and P; and/or each alkylene group may be optionally substituted by a group selected from hydroxyl, carboxy, aryl, and heteroaryl; and 2) an alkenyl silane (II) represented by the general formula

$$(R_1)_m X_{(3-m)} Si-R_2-R_3 \qquad (II)$$

wherein:
$R_1$ is a linear or branched $(C_1-C_{10})$alkyl group, which comprises optionally from 1 to 5 heteroatoms selected from $NR_4$ where $R_4$ represents a hydrogen atom or linear or branched $(C_1-C_6)$alkyl, O, S, and P; and/or each alkyl group may be optionally substituted by a group selected from hydroxyl, carboxy, and $(C_1-C_6)$alkoxy;

X is a group selected from a halogen atom, and $-OR_5$, wherein $R_5$ represents a group selected from $(C_3-C_{10})$cycloalkyl, $(C_3-C_{10})$heterocycloalkyl, and linear or branched $(C_1-C_6)$alkyl which may be comprised from 1 to 3 heteroatoms selected from the group consisting of $NR_4$ where $R_4$ represents a hydrogen atom or linear or branched $(C_1-C_6)$alkyl, O, S; and/or each alkyl group may be substituted by a group selected from linear or branched $(C_1-C_6)$alkoxy, carboxy, and hydroxy;

m is an integer between 0 and 2 inclusive;

$R_2$ is either absent or represented by a group selected from: linear or branched $(C_1-C_{10})$alkylene wherein from 1 to 4 carbon atoms may be replaced by a group selected from (CO), $NR_4$ where $R_4$ represents a hydrogen atom or linear or branched $(C_1-C_6)$alkyl, O, S; and/or each alkylene group may be optionally substituted by a group selected from linear or branched $(C_1-C_6)$alkoxy, carboxy, and hydroxy;

$R_3$ represents a group selected from linear or branched $(C_1-C_{10})$alkenyl, $(C_4-C_{10})$cycloalkenyl, and $(C_4-C_{10})$heterocycloalkenyl, each of these groups may be optionally substituted by a group selected from linear or branched $(C_1-C_6)$alkyl, linear or branched $(C_1-C_6)$alkoxy, linear or branched $(C_1-C_6)$thioalkoxy, carboxy, thiol, and hydroxyl.

2. The optical article of claim 1, wherein the polythiol (I) includes 2 to 6 thiol groups.

3. The optical article of claim 1, wherein in the polythiol (I), R comprises from 1 to 20 carbon atoms, and when a heteroatom is present in the R group, R represents a sulfur atom.

4. The optical article of claim 3, wherein in the polythiol (I), the ratio of S atoms to C atoms (nS/nC) is at least 1 over 4.

5. The optical article of claim 1, wherein in the polythiol (I), R comprises from 1 to 10 carbon atoms, and from 1 to 6 sulfur atoms, and wherein the ratio of S atoms to C atoms (nS/nC) is at least 1 over 2.

6. The optical article of claim 1, wherein in the alkenyl silane (II) m is zero, X is an alkoxy group, and $R_2$ is absent or represents a (C1-C3)alkylene group.

7. The optical article of claim 1, wherein the alkenyl silane (II) comprises vinyltrimethoxysilane.

8. An optical coating made from a hydrolyzed polysulfide polysilane (III), wherein the polysulfide polysilane(III) is obtained by the reaction of:

1) a polythiol (I) represented by the general formula, $$(HS)-R-(SH)_n \quad (I)$$

wherein n is an integer between 1 and 5 inclusive; and

R is a group selected from: arylene heteroarylene, and linear or branched ($C_1$-$C_{30}$)alkylene, wherein from 1 to 10 carbon atoms may be replaced by a group selected from (CO), ($SO_2$), $NR_4$ where $R_4$ represents a hydrogen atom or linear or branched ($C_1$-$C_6$)alkyl, O, S, and P; and/or each alkylene group may be optionally substituted by a group selected from hydroxyl, carboxy, aryl, and heteroaryl; and 2) an alkenyl silane (II) represented by the general formula $$(R_1)_m X_{(3-m)}Si-R_2-R_3 \quad (II)$$

wherein:

$R_1$ is a linear or branched ($C_1$-$C_{10}$)alkyl group, which comprises optionally from 1 to 5 heteroatoms selected from $NR_4$ where $R_4$ represents a hydrogen atom or linear or branched ($C_1$-$C_6$)alkyl, O, S, and P; and/or each alkyl group may be optionally substituted by a group selected from hydroxyl, carboxy, and ($C_1$-$C_6$)alkoxy;

X is a group selected from a halogen atom, and $-OR_5$, wherein $R_5$ represents a group selected from ($C_3$-$C_{10}$) cycloalkyl, ($C_3$-$C_{10}$)heterocycloalkyl, and linear or branched ($C_1$-$C_6$)alkyl which may be comprised from 1 to 3 heteroatoms selected from the group consisting of $NR_4$ where $R_4$ represents a hydrogen atom or linear or branched ($C_1$-$C_6$)alkyl, O, S; and/or each alkyl group may be substituted by a group selected from linear or branched ($C_1$-$C_6$)alkoxy, carboxy, and hydroxy;

m is an integer between 0 and 2 inclusive;

$R_2$ is either absent or represented by a group selected from: linear or branched ($C_1$-$C_{10}$)alkylene wherein from 1 to 4 carbon atoms may be replaced by a group selected from (CO), $NR_4$ where $R_4$ represents a hydrogen atom or linear or branched ($C_1$-$C_6$)alkyl, O, S; and/or each alkylene group may be optionally substituted by a group selected from linear or branched ($C_1$-$C_6$)alkoxy, carboxy, and hydroxy;

$R_3$ represents a group selected from linear or branched ($C_1$-$C_{10}$)alkenyl, ($C_4$-$C_{10}$)cycloalkenyl, and ($C_4$-$C_{10}$) heterocycloalkenyl, each of these groups may be optionally substituted by a group selected from linear or branched ($C_1$-$C_6$)alkyl, linear or branched ($C_1$-$C_6$) alkoxy, linear or branched ($C_1$-$C_6$)thioalkoxy, carboxy, thiol, and hydroxyl.

9. The optical coating of claim 8, wherein the coating includes nanoparticles.

10. The optical coating of claim 8, wherein the coating includes another silane that is mixed with the polysulfide polysilane (III), wherein said another silane is selected from the group consisting of glycidoxypropyltrimethoxysilane, another different polysulfide polysilane, and combinations thereof.

11. A polysulfide polysilane (III) obtained by the reaction of:

1) a polythiol (I) selected from the group comprising 1,2-ethanedithiol; 1,3-propanedithiol; 1,4-butanedithiol; 1,2-butanedithiol; 1,5-pentanedithiol; 1,6-hexanedithiol; 1,8-octanedithiol; 2,2'-oxydiethanethiol; 3,6-dioxa-1,8-octanedithiol; ethylene glycol bisthiolglycolate; dl-1,4-dithiothreitol; 2,2'-thiodiethanethiol; bis(2-mercaptoethyl)sulphone; 2,5-dimercapto-1,3,4-thiadiazole; 5-({2-[(5-mercapto-1,3,4-thiadiazol-2-yl) thio]ethyl}thio)-1,3,4-thiadiazole-2-thiol; pentaerythritol tetra(2-mercaptoacetate); trimethylolpropane tris (3-mercaptopropionate); trimethylolpropane tris (2-mercaptoacetate); 1,4-benzenedithiol; 1,3-benzenedithiol; 3,4-dimercaptotoluene; 1,4-benzenedimethanethiol; 1,3-benzenedimethanethiol; 1,6-di (methanethiol)-3,4-dimethyl-phenyl; [3-(mercaptomethyl)-2,4,6-trimethylphenyl] methanethiol; 1,5-dimercaptonaphthalene; 3,3'-thiobis [2-[(2-mercaptoethyl)thio]-1-propanethiol; 5-[3-(5-mercapto-1,3,4-oxadiazol-2-yl)propyl]-1,3,4-oxadiazole-2-thiol; 1,3,5-triazine-2,4,6(1H, 3H, 5H)-trithione; and 2,3-bis[(2-mercaptoethyl)thio]-1-propanethiol; and 2) an alkenyl silane (II) represented by the general formula $$(R_1)_m X_{(3-m)} Si-R_2-R_3 \quad (II)$$

wherein:

$R_1$ is a linear or branched ($C_1$-$C_{10}$)alkyl group, which comprises optionally from 1 to 5 heteroatoms selected from $NR_4$ where $R_4$ represents a hydrogen atom or linear or branched ($C_1$-$C_6$)alkyl, O, S, and P; and/or each alkyl group may be optionally substituted by a group selected from hydroxyl, carboxy, and ($C_1$-$C_6$)alkoxy;

X is a group selected from a halogen atom, and $-OR_5$, wherein $R_5$ represents a group selected from ($C_3$-$C_{10}$) cycloalkyl, ($C_3$-$C_{10}$)heterocycloalkyl, and linear or branched ($C_1$-$C_6$)alkyl which may be comprised from 1 to 3 heteroatoms selected from the group consisting of $NR_4$ where $R_4$ represents a hydrogen atom or linear or branched ($C_1$-$C_6$)alkyl, O, S; and/or each alkyl group may be substituted by a group selected from linear or branched ($C_1$-$C_6$)alkoxy, carboxy, and hydroxy;

m is an integer between 0 and 2 inclusive;

$R_2$ is either absent or represented by a group selected from: linear or branched ($C_1$-$C_{10}$)alkylene wherein from 1 to 4 carbon atoms may be replaced by a group selected from (CO), $NR_4$ where $R_4$ represents a hydrogen atom or linear or branched ($C_1$-$C_6$)alkyl, O, S; and/or each alkylene group may be optionally substituted by a group selected from linear or branched ($C_1$-$C_6$)alkoxy, carboxy, and hydroxy;

$R_3$ represents a group selected from linear or branched ($C_1$-$C_{10}$)alkenyl, ($C_4$-$C_{10}$)cycloalkenyl, and ($C_4$-$C_{10}$) heterocycloalkenyl, each of these groups may be optionally substituted by a group selected from linear or branched ($C_1$-$C_6$)alkyl, linear or branched ($C_1$-$C_6$) alkoxy, linear or branched ($C_1$-$C_6$)thioalkoxy, carboxy, thiol, and hydroxyl.

12. The polysulfide polysilane (III) of claim 11, wherein the alkenyl silane (II) comprises vinyltrimethoxysilane.

13. A polysulfide polysilane (III) obtained by the reaction of:

1) a polythiol (I) represented by the general formula, $$(HS)-R-(SH)_n \quad (I)$$

wherein n is an integer between 1 and 5 inclusive; and

R is a group selected from:
  arylene,
  heteroarylene,
  and linear or branched ($C_1$-$C_{30}$)alkylene, wherein from 1 to 10 carbon atoms may be replaced by a group selected from (CO), ($SO_2$), $NR_4$ where $R_4$ represents a hydrogen atom or linear or branched ($C_1$-$C_6$)alkyl, O, S, and P; and/or each alkylene group may be optionally substituted by a group selected from hydroxyl, carboxy, aryl, and heteroaryl; and 2) an alkenyl silane (II) represented by the general formula $$X_3Si\text{—}R_2\text{—}R_3 \tag{II}$$

wherein:

X is a linear or branched $(C_1-C_6)$alkoxy group;

$R_2$ is either absent or represented by a linear or branched $(C_1-C_3)$alkylene wherein each carbon atoms may be replaced by a group selected from (CO), $NR_4$ where $R_4$ represents a hydrogen atom or linear or branched $(C_1-C_6)$alkyl, O, S; and/or each alkylene group may be optionally substituted by a group selected from linear or branched $(C_1-C_6)$alkoxy, carboxy, and hydroxy;

$R_3$ represents a group selected from linear or branched $(C_1-C_{10})$alkenyl, $(C_4-C_{10})$cycloalkenyl, and $(C_4-C_{10})$heterocycloalkenyl, each of these groups may be optionally substituted by a group selected from linear or branched $(C_1-C_6)$alkyl, linear or branched $(C_1-C_6)$alkoxy, linear or branched $(C_1-C_6)$thioalkoxy, carboxy, thiol, and hydroxyl.

14. The polysulfide polysilane (III) of claim 13, wherein the alkenyl silane (II) comprises vinyltrimethoxysilane.

15. The optical coating of claim 8, wherein the polythiol (I) includes 2 to 6 thiol groups.

16. The optical coating of claim 8, wherein in the polythiol (I), R comprises from 1 to 20 carbon atoms, and when a heteroatom is present in the R group, R represents a sulfur atom.

17. The optical coating of claim 8, wherein in the polythiol (I), the ratio of S atoms to C atoms (nS/nC) is at least 1 over 4.

18. The optical coating of claim 8, wherein in the polythiol (I), R comprises from 1 to 10 carbon atoms, and from 1 to 6 sulfur atoms, and wherein the ratio of S atoms to C atoms (nS/nC) is at least 1 over 2.

19. The optical coating of claim 8, wherein in the alkenyl silane (II) m is zero, X is an alkoxy group, and $R_2$ is absent or represents a (C1-C3)alkylene group.

20. The optical coating of claim 8, wherein the alkenyl silane (II) comprises vinyltrimethoxysilane.

* * * * *